United States Patent [19]

Tombach

[11] 4,242,908
[45] Jan. 6, 1981

[54] PARTICULATE SAMPLER SHIELD

[75] Inventor: Ivar Tombach, Altadena, Calif.

[73] Assignee: Aerovironment Inc., Pasadena, Calif.

[21] Appl. No.: 52,096

[22] Filed: Jun. 26, 1979

[51] Int. Cl.$^3$ .............................................. G01N 1/24
[52] U.S. Cl. .............................................. 73/421.5 R
[58] Field of Search .................. 73/421.5 R, 421.5 A, 73/28, 170 R

[56] References Cited

U.S. PATENT DOCUMENTS

| | | | |
|---|---|---|---|
| 3,741,001 | 6/1973 | Fletcher | 73/28 |
| 4,117,715 | 10/1978 | Hoenig | 73/28 |

Primary Examiner—S. Clement Swisher
Attorney, Agent, or Firm—William W. Haefliger

[57] ABSTRACT

Shield structure usable with a particulate matter sampler having a particle size cut-off inlet, comprises:
(a) porous shield extending at least part way about said sampler inlet for reducing the velocity of gas flow reaching said inlet via the shield,
(b) said shield forming openings that pass the air and particulate entrained in the air for flow at reduced velocity within an open interior zone defined by the shield means and adapted to receive said sampler inlet.

11 Claims, 3 Drawing Figures

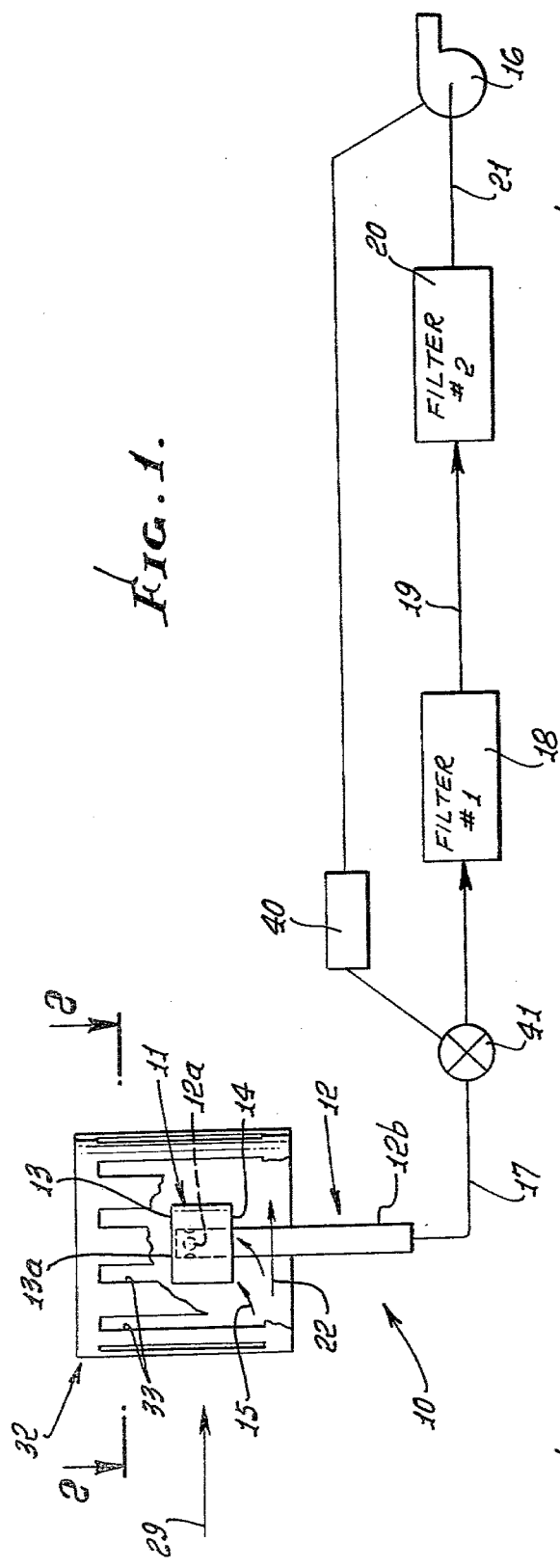
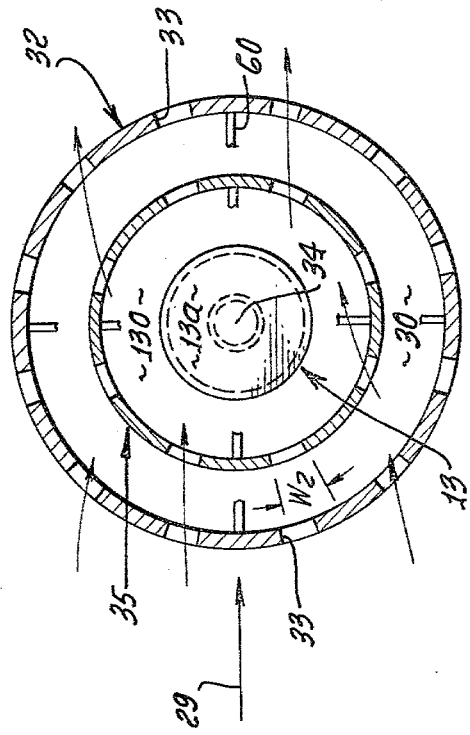
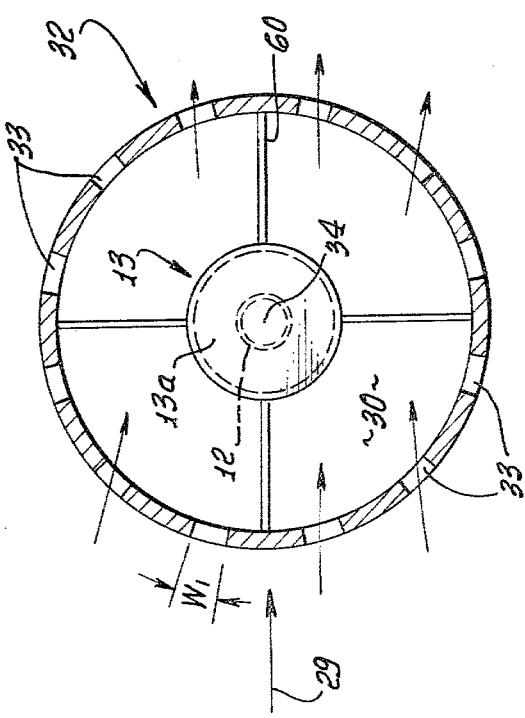

PARTICULATE SAMPLER SHIELD

BACKGROUND OF THE INVENTION

This invention relates generally to particulate sampling, and more specifically concerns an aerodynamic shield to alleviate wind-caused errors in particulate matter samplers.

Most devices which sample particulate matter (particles and drops in the size range of $<0.1\ \mu m$ to $>100\ \mu m$ diameter) in the air have an inlet which aerodynamically precludes particles which are larger than a certain size from entering the inlet. The sampler inlet design is usually such that the inertia of the larger particles prevents them from turning with the incoming airflow, or the gravitational settling speed of the larger particles is greater than the upward airflow speed into the inlet.

Such aerodynamic/inertial separation is frequently used intentionally to define the largest particles which the sampler will collect. Most inlet designs behave differently in still air than when the wind is blowing, however, and therefore the particle size cutoff of the inlet varies with the wind, often to a great degree.

SUMMARY OF THE INVENTION

It is a major object of the invention to provide apparatus to overcome the above difficulties and problems. In this regard it has now been found that the wind-speed dependence of the sampler inlet characteristics does not occur if the wind is decelerated sufficiently before reaching the sampler so that the inlet operates in essentially still air. The means used to decelerate the flow must not, however, change the particulate matter concentration or size distribution.

As will be seen the invention is embodied in a porous shield placed around the sampling head or inlet, the shield decelerating airflow effectively without creating strong shears which would affect the local particle size distribution. The porous shield allows the particles to pass through the shield in proportion to the airflow, preserving the particle concentration in the air.

Basically, then, the invention is useful in combination with a particulate matter sampler having an inlet providing particle size cut-off, and comprises (a) porous shield means extending at least part way about said sampler inlet for reducing the velocity of gas flow reaching said inlet via the shield means, (b) said shield means forming openings that pass the air and particulate entrained in the air for flow at reduced velocity within an open interior zone defined by the shield means and adapted to receive said sampler inlet.

As will appear, one or more shields may be provided about the sampler inlet, and they may have cylindrical configuration.

These and other objects and advantages of the invention, as well as the details of an illustrative embodiment, will be more fully understood from the following description and drawings in which:

DRAWING DESCRIPTION

FIG. 1 is an elevation showing one form of the invention;

FIG. 2 is an enlarged section taken on lines 2—2 of FIG. 1; and

FIG. 3 is a view like FIG. 2, showing a modification.

DETAILED DESCRIPTION

Shown in FIG. 1 is apparatus 10 to sample particulate matter in the air. The sampler includes a head 11 that includes a tube 12 having upperside holes 12a which admit the air sample; also, a cylindrical intake cap 13 surrounds the upper end portion of the tube, the top 13a of the cap being closed. As a result, a bottom annular inlet 14 is formed between the tube and cap to receive air and particulate as indicated by arrows 15. A suitable air displacement device such as a pump or blower 16 is connected with the tube to draw air into and from the tube via upward inlet 14, tube upper end 12a, tube body 12b, line 17, first filter 18, line 19, second filter 20, and line 21 connected to the pump inlet.

The sampler apparatus 10 collects dichotomous samples of air or gas aerosols, for example. Typically, particles smaller than a selected size (as for example about 15 $\mu m$ diameter) are drawn upwardly via inlet 14 and into the sampler, for separation on the two filters. Particles larger than the selected size are not drawn into the sampler, but flow generally horizontally with the air stream indicated by arrow 22 below inlet 14. First filter 18 typically stops particles larger than about 2.5 $\mu m$ (i.e. particle sizes that would collect in a person's nose and throat passages); and second filter 20 typically stops particles less than about 2.5 $\mu m$ (i.e. particle sizes that would pass through a person's nose and throat and lodge in the lungs (the lower respiratory tract). Accordingly, the sampler yields useful data on particulate size and concentration, in the ambient air stream, and the technique is inexpensive and highly advantageous. If, however, as above explained, the air or fluid flow velocity is not approximately constant, then the particle size "cut-off" characteristics of inlet 14 are not reliable.

In accordance with the invention, porous shield means is provided to extend at least part way about the sampler inlet for reducing the velocity of the approaching air or gas stream that reaches the inlet, via the shield means. The approaching air stream is indicated at 29 in FIG. 1. For that purpose, the shield means form openings that pass the air or gas particulate entrained in the air, at least up to the maximum size to be filtered at 18, but at the same time the openings slow the gas flow velocity, i.e. for example to "still air", or nearly still air, within the open interior zone 30 adjacent the cap 13 and interiorly of the shield means.

In the example, the shield means includes a first cylindrical shield 32 arrayed concentrically about the cylindrical cap 13, as seen in FIGS. 1 and 2. The shield 32 has vertical slots 33 spaced regularly about the common axis 34, and of a width "W$_1$" to pass all the particulate of interest, but also to slow down the air velocity in zone 30, so that the particulate of interest will enter the inlet 14, although larger particulate may not. FIG. 3 shows the same arrangement as in FIG. 2, but adds a second shield 35, like shield 32 but of smaller diameter. It too has slots of width "W$_2$" such that the air or gas flow velocity is slowed further. Two shields produce very good slowing of all approaching air velocities, to result in "still" or "near still" air or gas in zone 130 adjacent the cap 13. The widths of the shield portions between the slots are such that essentially all particles below the size cut-off selected will pass through the slots, and larger particles impinging on such shield portions tend to drop out.

Filters 18 and 20 may be suitably enclosed so as not to be exposed to ambient air. If desired, a single or multiple filters may be used. They may consist for example of Nuclepore filters. Also, a timer may be used to control the exposure of the filters to the flow in lines 17 and 19. For example, timer 40 may control the shut-off of valve 41 in line 17, and the shut-off of the blower 16.

The slots or openings in the shields 32 and 35 may have various forms. Those illustrated are spaced uniformly about axis 34, and extend vertically above and below the top and bottom of the cap 13, so that air approaching from any direction has full access to zones 30 and 130. The shield or shields pass essentially all particles below the cut-off size selected by the configuration of the inlet. The shields may be suitably supported at 60 on the cap 13.

I claim

1. For use in combination with a particulate matter sampler having an inlet providing particle size cut-off,
   (a) porous shield means extending at least part way about said sampler inlet for reducing the velocity of gas flow reaching said inlet via the shield means,
   (b) said shield means forming openings that pass the gas and particulate entrained in the gas for flow at reduced velocity within an open interior zone defined by the shield means and adapted to receive said sampler inlet, said open interior zone exposed to multiple of said openings and located generally radially inwardly of such openings and of the shield means between the openings.

2. The shield means of claim 1 that includes a first shield extending about said zone.

3. For use in combination with a particulate matter sampler having an inlet providing particle size cut-off,
   (a) porous shield means extending at least part way about said sampler inlet for reducing the velocity of gas flow reaching said inlet via the shield means,
   (b) said shield means forming openings that pass the air and particulate entrained in the air for flow at reduced velocity within an open interior zone defined by the shield means and adapted to receive said sampler inlet,
   (c) said shield means including a first shield extending about said zone, and also a second shield extending about said zone.

4. The combination that includes the shield means of any of claims 1–3, and that includes said sampler having said inlet in said zone.

5. The shield means of claim 1 which is cylindrical.

6. The first shield of claim 2 which is cylindrical.

7. The second shield of claim 3 which is cylindrical and concentric relative to the first shield.

8. The combination of claim 4 wherein said sampler also includes two filters arranged in series to separate two different size ranges of particulate, the said shield means openings characterized as passing all particulate in said size ranges.

9. The combination of claim 8 wherein said openings comprise narrow slots extending generally parallel to an axis defined by the shield means.

10. The combination of claim 9 wherein said size ranges are about:
    0 to 2.5 $\mu$m, and
    2.5 to 15 $\mu$m.

11. The combination of claim 1 wherein the shield means is configured to pass essentially all particles below the cut-off size selected by said inlet.

* * * * *